(12) United States Patent
Stoecker (10) Patent No.: US 9,977,040 B2
(45) Date of Patent: May 22, 2018

(54) DEVICE AND METHOD FOR REACTIONS BETWEEN A SOLID AND A LIQUID PHASE

(71) Applicant: EUROIMMUN MEDIZINISCHE LABORDIAGNOSTIKA AG, Luebeck (DE)

(72) Inventor: Winfried Stoecker, Gross Groenau (DE)

(73) Assignee: EUROIMMUN MEDIZINISCHE LABORDIAGNOSTIKA AG, Luebeck (DE)

( * ) Notice: Subject to any disclaimer, the term of this patent is extended or adjusted under 35 U.S.C. 154(b) by 0 days. days.

(21) Appl. No.: 15/032,193

(22) PCT Filed: Oct. 27, 2014

(86) PCT No.: PCT/EP2014/002889
§ 371 (c)(1),
(2) Date: Apr. 26, 2016

(87) PCT Pub. No.: WO2015/062715
PCT Pub. Date: May 7, 2015

(65) Prior Publication Data
US 2016/0258971 A1    Sep. 8, 2016

(30) Foreign Application Priority Data

Oct. 28, 2013 (DE) .......................... 10 2013 017 802
Feb. 6, 2014 (DE) .......................... 10 2014 001 481

(51) Int. Cl.
*G01N 35/00* (2006.01)
*G02B 21/34* (2006.01)
(Continued)

(52) U.S. Cl.
CPC ........ *G01N 35/00029* (2013.01); *B01L 3/502* (2013.01); *B01L 9/52* (2013.01);
(Continued)

(58) Field of Classification Search
CPC .. G01N 35/00029; G01N 1/312; G01N 35/10; B01L 3/502; B01L 9/52; G02B 21/34
(Continued)

(56) References Cited

U.S. PATENT DOCUMENTS 4,274,359 A * 6/1981 Di Maggio, Jr. ...... G01N 1/312
                                                                118/326
4,647,543 A   3/1987 Winfried Stoecker
(Continued)

FOREIGN PATENT DOCUMENTS

DE        202 20 299 U1   7/2003
DE    20 2008 001 277 U1   6/2008
(Continued)

OTHER PUBLICATIONS

International Search Report dated Jan. 23, 2015 for PCT/EP2014/002889 filed on Oct. 27, 2014.
(Continued)

*Primary Examiner* — Jill A Warden
*Assistant Examiner* — Jacqueline Brazin
(74) *Attorney, Agent, or Firm* — Grüneberg and Myers PLLC (57) ABSTRACT

The invention relates to a device for bringing an immobilized reactant into contact with at least one fluid, said device comprising: a basin having a bottom surface from which an upper side of at least one elevated portion projects into the interior of the basin, and said at least one elevated portion having a channel running, preferably perpendicular to the bottom surface of the basin, from the bottom surface of the basin to the upper side of the portion, and leading into at least one outlet opening on the upper side of the elevated portion, wherein the channel is fed from at least one fluid reservoir via a supply element by means of a pump device, (Continued)

said reservoir containing the at least one fluid; a holding device designed to detachably hold at least one object carrier, preferably a plurality of object carriers, having at least one surface of adhesion to the immobilized reactant, in such a way that the adhesion surface is facing the interior of the basin, and the upper side of the elevated portion and the adhesion surface are positioned relative to one another in such a way that fluid exiting the outlet opening comes into contact with the immobilized reactant; and optionally an object carrier introduced into the holding device. The invention also relates to a method for bringing an immobilized reactant into contact with at least one fluid, comprising the following steps: immobilizing the reactant on the adhesion surface of at least one object carrier suitable for introduction into the holding device of the device according to the invention; (provided that the preceding steps were carried out outside of the device according to the invention) introducing the object carrier into the holding device of the device according to the invention, preferably via a transport device in the device according to the invention; introducing the at least one fluid via the supply element in the direction of the outlet opening, until the at least one fluid comes into contact with the immobilized reactant.

25 Claims, 4 Drawing Sheets

(51) Int. Cl.
| | | |
|---|---|---|
| *G01N 35/10* | (2006.01) | |
| *G01N 1/31* | (2006.01) | |
| *B01L 3/00* | (2006.01) | |
| *B01L 9/00* | (2006.01) | |
| *G01N 1/28* | (2006.01) | |
| *G01N 33/552* | (2006.01) | |

(52) U.S. Cl.
CPC .............. *G01N 1/312* (2013.01); *G01N 35/10* (2013.01); *G02B 21/34* (2013.01); *B01L 2300/06* (2013.01); *B01L 2300/0609* (2013.01); *B01L 2300/0848* (2013.01); *B01L 2300/0861* (2013.01); *G01N 1/2813* (2013.01); *G01N 33/552* (2013.01); *G01N 2035/00138* (2013.01); *G01N 2035/00158* (2013.01)

(58) Field of Classification Search
USPC ........................................................ 436/169
See application file for complete search history.

(56) References Cited

U.S. PATENT DOCUMENTS

| | | |
|---|---|---|
| 4,847,208 A | 7/1989 | Bogen |
| 5,068,091 A | 11/1991 | Toya |
| 5,188,963 A | 2/1993 | Stapleton |
| 5,436,129 A | 7/1995 | Stapleton |
| 5,451,500 A | 9/1995 | Stapleton |
| 5,981,733 A | 11/1999 | Gamble et al. |
| 6,534,008 B1 | 3/2003 | Angros |
| 2003/0003504 A1 | 1/2003 | Bass et al. |
| 2003/0017075 A1 | 1/2003 | Angros |
| 2003/0170144 A1 | 9/2003 | Angros |
| 2004/0086428 A1 | 5/2004 | Loeffler et al. |
| 2005/0053526 A1 | 3/2005 | Angros |
| 2005/0054079 A1 | 3/2005 | Angros |
| 2005/0054080 A1 | 3/2005 | Angros |
| 2006/0239858 A1 | 10/2006 | Becker |
| 2007/0231889 A1 | 10/2007 | Angros |
| 2008/0318305 A1 | 12/2008 | Angros |
| 2009/0011425 A1 | 1/2009 | Delaage et al. |
| 2009/0117611 A1 | 5/2009 | Becker et al. |
| 2009/0270599 A1 | 10/2009 | Angros |
| 2010/0009429 A1 | 1/2010 | Angros |
| 2010/0068096 A1 | 3/2010 | Angros |
| 2010/0068102 A1 | 3/2010 | Angros |
| 2010/0124750 A1 | 5/2010 | Stoecker et al. |
| 2011/0312085 A1 | 12/2011 | Angros |
| 2011/0318825 A1 | 12/2011 | Angros |
| 2012/0058570 A1 | 3/2012 | Angros |
| 2012/0107198 A1 | 5/2012 | Angros |
| 2012/0149050 A1* | 6/2012 | Lapen .............. G01N 35/00029 435/29 |
| 2013/0130366 A1 | 5/2013 | Angros |
| 2014/0004561 A1 | 1/2014 | Lapen et al. |
| 2014/0093893 A1 | 4/2014 | Angros |
| 2014/0227714 A1 | 8/2014 | Angros |

FOREIGN PATENT DOCUMENTS

| | | |
|---|---|---|
| EP | 0 117 262 A1 | 9/1984 |
| EP | 0 270 363 A2 | 6/1988 |
| EP | 2 053 378 A2 | 4/2009 |
| EP | 2053378 * | 4/2009 |
| EP | 2 191 893 A1 | 6/2010 |
| WO | 01/04634 A1 | 1/2001 |
| WO | WO 01/31347 A1 | 5/2001 |
| WO | WO 2005/016532 A2 | 2/2005 |

OTHER PUBLICATIONS

Office Action dated Oct. 21, 2014 in German Patent Application No. 10 2014 001 481.9 (with English language translation).
International Preliminary Report on Patentability and Written Opinion dated May 3, 2016 in PCT/EP2014/002889.

* cited by examiner

DEVICE AND METHOD FOR REACTIONS BETWEEN A SOLID AND A LIQUID PHASE

The present invention relates to a device for contacting an immobilized reaction partner with at least one liquid, comprising a trough having a base from which at least one elevation having an upper side projects into the interior of the trough, wherein the at least one elevation has a channel which runs from the base of the trough to the upper side of the elevation, preferably perpendicularly to the base of the trough, and opens into at least one escape opening on the upper side of the elevation, wherein the channel is fed from at least one liquid reservoir containing the at least one liquid via a feed element by means of a pumping device, a holding device configured to detachably hold at least one microscope slide, preferably a multiplicity of microscope slides, having at least one adhesion surface containing the immobilized reaction partner, such that the adhesion surface is facing the interior of the trough, and that the upper side of the elevation and the adhesion surface are positioned relative to one another such that liquid escaping from the escape opening is in contact with the immobilized reagent, wherein the device optionally comprises a microscope slide inserted into the holding device, and also to a method for contacting an immobilized reaction partner with at least one liquid, comprising the steps of a) immobilizing the reaction partner on the adhesion surface of at least one microscope slide suitable for insertion into the holding device of the device according to the invention, b) if the prior steps were carried out outside the device according to the invention: inserting the microscope slide into the holding device of the device according to the invention, preferably via a transport device in the device according to the invention, c) introducing the at least one liquid in the direction of the escape opening via the feed element until the at least one liquid is in contact with the immobilized reaction partner.

Numerous analytical methods in the fields of chemistry, biology and medicine, especially in the area of medical laboratory diagnostics, are based on the fact that an individual reactant, for example an autoantibody, in a complex sample mixture is detected via its specific interaction with a reaction partner, for example an antigen. Said specific interaction can be detected most efficiently when substances other than the reactant and its reaction partner are present in very low concentrations. For this reason, the reaction partner is frequently immobilized via a covalent or reversible chemical bond, said reaction partner is then incubated with the sample mixture which might contain the individual reactant, and the reactant-depleted sample mixture is lastly removed, leaving the complex composed of the reactant to be detected and the reaction partner. Said complex can be detected using customary detection methods such as fluorescence, spectroscopy or color reactions.

An example of such an analytical detection method is the classic ELISA (enzyme-linked immunosorbent assay), which can be carried out by firstly immobilizing any reaction partner recognized by an antibody, for example a peptide or a protein. Thereafter, a sample mixture which might contain the antibody to be detected is contacted with the immobilized reaction partner in aqueous solution under conditions conducive to the formation of a complex. After removal of the sample mixture, the complex between the immobilized antigen and the antibody is detected via a second, enzyme-labeled antibody which can catalyze a color reaction.

Crucial to the sensitivity and specificity of the detection is the purity of the complex composed of immobilized reaction partner and reactant. Additional, contaminating substances from the sample mixture can interfere with the physical detection of the complex by, for example, emitting in wavelength ranges similar to those of the complex in fluorescence measurements. A chemical degradation of the complex, too, is possible. For example, human serum contains reactive components such as proteases, which can degrade protein constituents of the complex. Therefore, the complex must be cleared of contaminating substances very efficiently by means of wash steps.

Whereas other steps of such analytical methods, for example the immobilization of the reaction partner and the contacting with detection reagents, can by now be carried out in an automated manner in high-throughput methods, the wash steps, especially in the case of complex molecules or sensitive tissues as immobilized reaction partners, are at present still carried out manually to a large extent. To this end, microscope slides are usually removed by hand from the analysis instrument and placed into a wash solution-containing trough together with other microscope slides from parallel batches.

However, one individual step carried out manually is enough to reduce very considerably the efficiency of the analytical high-throughput methods. Since the presence of a trained specialist is required, the workflows accordingly need complicated planning. For example, it is not possible to let the method run unattended overnight and to merely take note of the final result at any time the following day.

The conventional manual process for wash steps has further disadvantages. If multiple microscope slides are being washed together in a trough, there is the risk of contamination when, as a result of diffusion, reactants to be detected also come into contact with immobilized reaction partners which had previously been contacted with a sample that did not contain any reactants. This can lead to a high fluorescence background, which complicates the evaluation, or in the worst case to false results.

The volume of the wash solution must be large enough for said solution to cover the entire microscope slide, increasing the resource requirements of the method in the case of wash steps carried out manually.

The individual microscope slides must be additionally dried for a range of detection methods, and this again mainly takes place manually. In this connection, the manual process brings about the possibility of drying steps being carried out too late, in a poorly reproducible manner or in an incomplete manner. As a result, the quality of the reaction partner or of the detection method can suffer when, for instance in the case of delayed drying, evaporating buffer solutions form salt crystals or aqueous biological samples decay owing to microbial colonization and contamination.

The prior art, for example US2006239858, describes devices by means of which a microscope slide is immersed upside down into a trough containing liquid, i.e., with the side on which the sample to be investigated has been immobilized facing down. Such devices only allow the separate processing of individual samples, but do not allow an increase in efficiency in the case of parallel processing of a multiplicity of samples. If nothing else, the problem of the volume of the solution into which the microscope slide must be immersed needing to be large enough for at least one side of the microscope slide to be completely covered remains unsolved.

Against this background, it is an object of the present invention to provide a device which makes it possible to contact in parallel an immobilized reaction partner in multiple separate batches with various liquids, more particularly with a wash liquid, in succession in each case and to subsequently dry said immobilized reaction partner, without reagents or liquids from separate batches being mixed while this is being done.

It is a further object of the present invention to provide a device for carrying out analytical detection methods, wherein the space requirements, the consumption of liquid and/or the duration are reduced with respect to the methods described in the prior art, whereas the reproducibility is increased.

It is a further object of the present invention to provide a device for carrying out analytical detection methods, wherein the susceptibility of the detection to interference, for example due to solids present in the sample or due to artifacts, is reduced, especially when the detection is carried out by means of immunofluorescence.

These objects and further objects are achieved by the subject matter of the present application and especially also by the subject matter of the accompanying independent claims, with embodiments being revealed by the dependent claims.

In a first aspect, the object underlying the invention is achieved by a device for contacting at least one immobilized reaction partner with at least one liquid, comprising a trough having a base from which at least one elevation having an upper side projects into the interior of the trough, wherein the at least one elevation has a channel which runs from the base of the trough to the upper side of the elevation, preferably perpendicularly to the base of the trough, and opens into at least one escape opening on the upper side of the elevation, wherein the channel is fed from at least one liquid reservoir containing the at least one liquid via a feed element by means of a pumping device, a holding device configured to detachably hold at least one microscope slide having at least one adhesion surface containing the at least one immobilized reagent, such that the adhesion surface is facing the interior of the trough, wherein the upper side of the elevation and the adhesion surface are positioned in relation to one another and such that liquid escaping from the escape opening is in contact with the immobilized reagent, wherein the device optionally comprises at least one microscope slide inserted into the holding device.

In a first embodiment of the first aspect, the object is achieved by a device, wherein the channel is additionally fed from a further liquid reservoir containing a second liquid.

In a second embodiment, which also represents one embodiment of the first embodiment of the first aspect, the object is achieved by a device, wherein the channel opens into more than one escape opening on the upper side of the elevation.

In a third embodiment, which also represents one embodiment of the first to second embodiments of the first aspect, the object is achieved by a device, wherein the adhesion surface has a central point and the upper side of the elevation has a central point, and wherein the central point of the adhesion surface and the central point of the upper side of the elevation are opposite each other.

In a fourth embodiment, which also represents one embodiment of the first to third embodiments of the first aspect, the object is achieved by a device, wherein the trough has at least one drain opening.

In a fifth embodiment, which also represents one embodiment of the first to fourth embodiments of the first aspect, the object is achieved by a device, wherein the holding device allows a movement of the microscope slide, preferably along the longitudinal axis of the trough, preferably over at least one groove or rail applied to the upper edges of the trough.

In a sixth embodiment, which also represents one embodiment of the first to fifth embodiments of the first aspect, the object is achieved by a device, wherein the trough is further provided with at least one air nozzle for drying the adhesion surface, and wherein the air stream from the at least one air nozzle preferably forms an angle (W) of less than 90 degrees, preferably from 20 to 70 degrees, with the plane determined by the base of the trough.

In a seventh embodiment, which also represents one embodiment of the first to sixth embodiments of the first aspect, the object is achieved by a device, wherein the pumping device allows liquid which is in contact with the immobilized reaction partner to be aspirated from the direction of the escape opening.

In an eighth embodiment, which also represents one embodiment of the first to seventh embodiments of the first aspect, the object is achieved by a device, further comprising a transport device which allows the insertion of the microscope slide into the device.

In a ninth embodiment, which also represents one embodiment of the first to eighth embodiments of the first aspect, the object is achieved by a device, wherein the escape opening on the upper side of the elevation, the upper side of the elevation and the adhesion surface are designed such that the at least one liquid flows tangentially along the immobilized reaction partner when said liquid is introduced into the device.

In a tenth embodiment, which is also one embodiment of the first to ninth embodiments, the holding device comprises a frame equipped to accommodate and to hold the at least one microscope slide, preferably a multiplicity of microscope slides, wherein, after accommodation, the adhesion surface is situated on that side of the microscope slide which is resting on the frame.

In a second aspect, the object underlying the invention is achieved by a holding device comprising a frame equipped to accommodate at least one microscope slide, preferably a multiplicity of microscope slides, wherein the microscope slide has at least one adhesion surface containing an immobilized reaction partner, wherein, after accommodation, the adhesion surface of the microscope slide is situated on that side of the microscope slide which is resting on the frame, and wherein, after accommodation, the adhesion surface is positioned such that it is accessible to a contact with liquid escaping from the escape opening.

In a first embodiment of the second aspect, the holding device comprises the microscope slide.

In a preferred embodiment, the frame has at least one lateral wall which is preferably provided with a handle, wherein the lateral wall of the frame has even more preferably a profile suited to positioning the holding device and thus the adhesion surface in the device.

In a third aspect, the object underlying the invention is achieved by a method for contacting at least one immobilized reaction partner with at least one liquid, comprising the steps of a) providing the device according to the invention comprising the at least one microscope slide containing immobilized reaction partner, and b) introducing the at least one liquid in the direction of the escape opening via the feed element until the at least one liquid is in contact with the immobilized reaction partner.

In a first embodiment of the third aspect, the object is achieved by a method comprising the step of c) introducing a second liquid and optionally a further liquid in the direction of the escape opening via the feed element until the second liquid is in contact with the immobilized reaction partner.

In a second embodiment, which also represents one embodiment of the first embodiment of the third aspect, the object is achieved by a method further comprising the step of d) introducing a wash solution in the direction of the escape opening via the feed element until the wash solution is in contact with the immobilized reaction partner, wherein step d) can be carried out before and/or after each of steps a), b), and c).

In a third embodiment, which represents one embodiment of the second embodiment of the third aspect, the object is achieved by a method, wherein the introduction of the wash solution is carried out until the device according to the invention has been completely cleared of contaminants.

In a third embodiment, which also represents one embodiment of the first to second embodiments of the third aspect, the object is achieved by a method, wherein the introduction of the at least one liquid, the second liquid and optionally further liquid and/or wash solution, preferably the introduction of both the at least one and second liquid and the wash solution, is followed by an additional step of e) aspirating the at least one or second liquid and optionally further liquid or the wash solution from the immobilized reaction partner from the direction of the adhesion surface via the channel.

In a fourth embodiment, which also represents one embodiment of the first to third embodiments of the third aspect, step a) comprises the accommodation of the at least one microscope slide in the holding device according to the invention comprising a frame and the subsequent insertion of the holding device into the device according to the invention.

The present invention provides a method for contacting at least one immobilized reaction partner with at least one liquid, preferably for immunological, histochemical and cytochemical, molecular biology-based, enzymological, pharmacological and clinical chemistry-based detection methods, and requires firstly a trough. In a preferred embodiment, the trough is a vessel of any construction having a base which is preferably surrounded by upright, preferably perpendicular, walls which close off an interior of the trough from the environment, which vessel is suited to housing, firstly, the microscope slide via the holding device and, secondly, the elevations projecting into its own interior. For example, the trough is a trough having a rectangular base area, a bowl or a can. Preferably, the trough is watertight, so liquid may trickle down from the elevations or is sprayed in the interior of the trough without escaping in an uncontrolled manner. Typically, the trough is produced from a chemically inert, easy-to-clean and easy-to-handle plastic, for example from Plexiglas. The base can be inclined relative to the gravitational field of Earth such that liquid falling on the incline accordingly flows off, preferably in the direction of an outlet opening optionally present. The trough can be open or be closable with a lid, a flap or the like. In the case of light-sensitive immobilized reaction partners, reactants or liquids, the trough can be nontransparent.

The microscope slide to be used according to the invention and the trough are functionally adapted to one another. In a preferred embodiment, the term "microscope slide", as used here, is understood to mean a structural element which is adapted to the trough and which serves the purpose of presenting the immobilized reaction partner in a form accessible to introduced liquid. For example, suitable microscope slides are described in DE 20 2011 005 278. Typically, according to the invention, the microscope slide comprises a base body composed of glass, but it is in principle also possible to use other supports which have deviating shapes and are composed of different materials, for example plastics. The microscope slide has at least one, preferably at least or precisely two, three, four, five, six, eight, 10, 12, 16, 20, 30, 40 or 50 adhesion surfaces separated from one another. In a preferred embodiment, the term "adhesion surface", as used here, is understood to mean a field on the microscope slide, which field is suited to immobilizing the reaction partner, either directly or via an additional support. For this purpose, the adhesion surface can have reactive or activatable chemical functions suited to the formation of covalent bonds in relation to a reaction partner to be immobilized. Alternatively, the adhesion surface can be provided such that the reaction partner to be immobilized is immobilized via hydrophobic interactions. Lastly, the immobilization can be achieved by fixing a further support, for example a biochip, on the adhesion surface, for example by adhesion. The production of such biochips is described in the prior art, for example in EP 0 117 262, as are devices and methods for the largely automated production of suitable microscope slides, for example in WO2005073693. Geometrically, the adhesion surface can be in the plane determined by the base area of the microscope slide, opposite it or else elevated or lowered. The adhesion surface is preferably parallel to the base area of the microscope slide.

According to the invention, the microscope slide and the trough can be held in contact with one another via a holding device which causes them to be in a defined, determined position in relation to one another, more particularly at a determined distance. For this purpose, microscope slide and trough can comprise protrusions and indentations that are assigned to one another, snap-in elements and/or stops. Because the microscope slide is upside down, i.e., with the adhesion surface facing the base of the trough, solids in a solution in contact with the adhesion surface fall by gravity and, especially in the case of directed flow due to introduced liquid, do not contaminate the complex composed of immobilized reaction partner and reactant. Furthermore, microscope slide and trough can be detachably connected to one another via suitable means, for example clamps, interlock buttons or the like. In a preferred embodiment, microscope slide and trough are not irreversibly fixed to one another via the holding device, but are instead held together in a detachable manner.

A further essential element of the invention is the at least one elevation which projects from the base of the trough into the interior thereof and which has the escape opening via which the at least one liquid from the liquid reservoir can reach the upper side of the elevation via the feed element and the channel. After insertion of the microscope slide, the upper side of said elevation is situated close to the adhesion surface, preferably within a short distance which allows a simultaneous wetting of the upper side of the elevation and of the adhesion surface by liquid escaping from the escape opening, particularly preferably such that the interspace, when the adhesion surface is in contact with a liquid, between upper side of the elevation and adhesion surface can be completely filled with liquid. For example, the distance between upper side of the elevation and adhesion surface is 0.05 to 3.00 mm. Preferably, the upper side of the elevation and the adhesion surface are hydrophilic and completely wettable by aqueous liquid. Furthermore, it is preferred that the upper side of the elevation and the adhesion surface are arranged in parallel to one another and are, even more preferably, planar. In a preferred embodiment, the device according to the invention has a multiplicity of such elevations and can simultaneously process a corresponding number of adhesion surfaces, for example at least or precisely 2, 4, 8, 16, 24, 30, 40, 50, 100, 200, 250, 300, 400, 500, 600, 700, 750, 800, 900 or 1000 elevations. In a preferred embodiment, the device according to the invention has two or more elevations and accordingly two or more corresponding adhesion surfaces, and these are shaped and situated at a sufficient distance from one another such that the liquid introduced through the elevations does not come into contact with adhesion surfaces which are situated opposite adjacent elevations.

The device according to the invention is provided such that liquid escaping from the escape opening on the upper side of the elevation comes into contact with the adhesion surface. In a preferred embodiment, the term "come into contact" is understood to mean that escaping liquid is in contact with the immobilized reaction partner such that chemical reactions can proceed between a reactant present in the liquid and the immobilized reaction partner. In a particularly preferred embodiment, the liquid is, in this connection, in contact with the upper side of the elevation and with the adhesion surface at the same time. In a further preferred embodiment, the liquid is, at the time of reaction of a reactant present therein, in contact with the immobilized reaction partner, but not with the upper side of the elevation. For example, this is the case when the escape opening, the distance between upper side of the elevation and adhesion surface, and the pressure with which the liquid escapes from the escape opening are dimensioned such that the liquid escapes in one stream and the adhesion surface is sprayed.

The elevation having the escape opening can be fixed on the base of the trough in a static or mobile manner. In the case of a mobile elevation, the elevation can move along multiple adhesion surfaces, or an elongated adhesion surface, in a sequential or successive manner and contact each of them with the at least one liquid.

The upper side of the elevation can comprise one escape opening, or else more than one escape opening. In the case of the latter, it is preferred that the escape openings are evenly distributed on the upper side of the elevation. They can be fed via one channel which branches before the escape openings, or via more than one channel from the one or more than one liquid reservoir. In a particularly preferred embodiment, the trough has two or more than two elevations, and the one or more than one escape opening of each elevation is in each case fed by its own system comprising at least one channel, at least one feed element, at least one pumping device and at least one liquid reservoir. It is then possible to contact multiple batches containing immobilized reaction partner at the same time with various liquids.

For automation and better reproducibility, it is advantageous when the at least one liquid is pumped to the upper side of the elevation from the liquid reservoir via a suitable pumping device. In a preferred embodiment, one or more than one pump is provided to this end. The pumping device is preferably provided such that it is possible for the at least one liquid to be not only introduced, but also aspirated. For example, separate pumps can be provided for introduction and aspiration, or one pump having a reversible pumping direction.

The liquid reservoir used can be any vessel suitable for the temporary or extended storage of the liquid to be introduced. In the case of a wash solution, a large-volume supply vessel is useful, for example a glass or plastic bottle. In the case of liquids available in smaller volumes, for example liquid samples of human or animal origin, smaller dimensioned vessels are accordingly suitable, for example test tubes, microliter tubes, centrifuge tubes, capillaries or the like. Preferably, a sample can be introduced into the device according to the invention from a transport container or from a device suitable for collecting the sample, for example a syringe.

It is especially advantageous when more than one liquid reservoir is connected to the channel such that two or more than two different liquids can be introduced successively or simultaneously with a freely selectable mixing ratio, for example a liquid containing a reactant, a wash solution and/or a second liquid. Possible feed elements include tubing, pipes and the like. The liquid reservoir can be adjustable in temperature in order to ensure conditions which are optimal for detection methods and reproducible.

The holding device serves the purpose of determining the relative position of trough and microscope slide to one another. It can be integrated in the device, preferably in a nondetachable manner. In a preferred embodiment, the trough has one or more than one microscope slide support surface for accommodating the microscope slide, which support surface preferably starts in the edge region of the microscope slide at a sufficient distance from the adhesion surface. Preferably, two microscope slide support surfaces which lie or are fixed on opposing walls of the trough, even more preferably microscope slide support surfaces which lie on the upper edges of the walls, can allow the insertion of the microscope slide into the device according to the invention by having it put down on two of its opposing edges or two of its opposing corners. Alternatively, the microscope slide can be detachably fixed on one side via a clamp or a gripper. Preferably, the holding device ensures that the microscope slide can only move along the longitudinal axis of the trough. If such a movement along the longitudinal axis is desired, microscope slide and trough can be provided with a motion system, for example wheels and rails. In a further embodiment, the position of the microscope slide, after insertion into the trough, can be fixed, and so the microscope slide rests in an immovable manner. The holding device can also allow the vertical raising or lowering of the microscope slide, optionally also comprising one or more than one ventilator.

In a preferred embodiment, the holding device is not integrated in a nondetachable manner in the device according to the invention, but is instead provided as a separate part which can accommodate at least one microscope slide, preferably a multiplicity of microscope slides, and serves the purpose of inserting said microscope slide(s) into the device and of positioning them in order to carry out the method according to the invention. In a preferred embodiment, the holding device comprises a frame equipped to accommodate and to hold the microscope slide, and, after accommodation, the adhesion surface is situated on that side of the microscope slide which is resting on the frame.

In a preferred embodiment, the device according to the invention or the holding device is equipped to accommodate and to hold more than one microscope slide, preferably a multiplicity of microscope slides, for example 2, 3, 4, 6, 8, 10, 12, 14, 16, 20, 24, 28, 30, 32, 36, 40, 50, 60, 70, 80, 90, 100, 200, 300, 400, 500 or 1000 microscope slides. When carrying out the method, it must be ensured that each adhesion surface on a microscope slide that is to be contacted with liquid is positioned relative to an elevation in a manner appropriate for this purpose. Preferably, one elevation is available for each adhesion surface to be contacted with liquid. However, it is also possible for one elevation to provide the liquid for more than one adhesion surface or for one adhesion surface to be contacted with liquid by more than one elevation.

The frame can comprise means for the reversible or irreversible fixing of the microscope slides on the frame, for example indentations into which the microscope slide is inserted such that its adhesion surface points in the direction of the elevations, i.e., downward, when the holding device is inserted into the device according to the invention from above. The microscope slide can be inserted by mere placement on the frame or fixing, for example with clamps or the like.

The exact position of the holding device in the device according to the invention can be determined by the shape of the former, especially by the profile of its lateral walls, if present, and is dimensioned such that the distance between the upper side of the elevation and the adhesion surface allows the performance of the method according to the invention. After performance, the holding device containing the microscope slide can be removed and, if necessary, replaced by a further holding device containing another microscope slide. This makes it possible, especially in the case of a multiplicity of microscope slides to be processed, to prepare during the method the next set of microscope slides in parallel to the currently running process and to then insert said set into the device in a simple and time-saving manner.

For many applications, it is possible to insert the microscope slide manually into the trough. In the case of a device according to the invention designed for automated high-throughput methods, it is, however, preferred that the device has a transport device which automatically inserts the microscope slide or the holding device containing the microscope slide from a storage unit or incubation unit into the trough.

In a preferred embodiment, the trough can be sealed in a pressure-tight manner in the presence or absence of the microscope slide, and so liquids are removed by application of a negative pressure or pushed out of the device via positive pressure. Particularly preferably, channel, feed element and, if present, drain opening and further openings can be sealed in a pressure-tight manner, for example via suitable stopcocks. A pressure-tight seal also allows the installation of a gas mixing station which can generate within the trough a gas atmosphere having a selectable composition, for example an atmosphere having at least one inert gas selected from the group comprising nitrogen, noble gases and carbon dioxide for substances sensitive to oxygen. In the case of other applications in which the presence of air does not have an interfering effect or is even desired, for example because air components such as oxygen are required for chemical detection reactions, the device according to the invention can have one or more than one opening for gas exchange with the environment.

According to the invention, it is necessary for the reaction partner to be immobilized. In a preferred embodiment, the term "reaction partner", as used here, is understood to mean a molecule which, because of its chemical nature, is suited to being immobilized and at the same time, even in the immobilized state, to forming a specific interaction with a given reactant present in liquid. For example, the immobilized reaction partner can be a peptide or polypeptide, a natural substance, an artificial polymer or a nucleic acid, preferably DNA, or a modification or hybrid thereof, and can similarly be a molecular complex, for example a protein composed of multiple subunits, or a substrate selected from the group comprising thin sections of biological tissue, cell smears of mammalian cells, bacteria or smears thereof, viruses, protozoa and parasites. The reaction partner can be used in enriched form right up to virtually complete purity, but also in the form of a mixture, if this does not greatly impair the formation of the interaction in relation to the reactant. Methods for purifying typical reaction partners such as nucleic acids, natural substances or polypeptides are known to a person skilled in the art. It is possible to immobilize more than one reaction support, for example at least or precisely two, three, four or 5 reaction partners on an adhesion surface.

The at least one liquid can be any desired liquid which is to be contacted with the adhesion surface on the microscope slide. In a preferred embodiment, the liquid is a liquid containing at least one reactant or, even more preferably, a liquid in which, as part of an analytical and/or diagnostic method, the intention is to establish whether and, optionally, in which concentration the reactant is present therein. In a preferred embodiment, the term "reactant", as used here, is to be understood to mean a molecule, a complex, a structure, a cell or the like capable of binding to the or reacting with the immobilized reaction partner. For example, the reactant can be a protein such as an antibody or an intercalating protein, a nucleic acid, a small molecule or a natural substance. The identification and, if necessary, preparation of reactants for various reaction partners is familiar to a person skilled in the art and described in the prior art. For example, antibodies for a polypeptide antigen can be prepared by immunization of a mammal. The liquid can also contain a mixture comprising more than one reactant.

In a preferred embodiment, the at least one or second liquid is a sample of human or animal origin that contains a reactant to be detected, for example a metabolite, a protein, a nucleic acid having a particular sequence or an antibody, preferably an autoantibody. Particularly preferably, the sample is a sample comprising a body fluid selected from the group comprising serum, urine, cerebrospinal fluid or saliva or a dilution or processed form thereof. Alternatively, the sample can be a sample from foodstuffs, beverages, drinking or bath water, stool, soil material or the like. Preferably, the sample is appropriately processed after acquisition, for example by centrifugation of insoluble blood constituents in the case of a blood sample, and/or preserved. Processing can also comprise chemical reactions and derivatizations proceeding from a sample as educt, for example the performance of a polymerase chain reaction to replicate a nucleotide sequence to be detected in the sample.

In a further preferred embodiment, the at least one liquid or second liquid is a wash solution. Wash solutions serve the purpose of clearing parts of the device according to the invention, such as the upper side of the elevation, the adhesion surface with or without the immobilized reaction partner, the channel and/or the feed element, of undesired substances, for example undesired constituents of liquid samples which are not usable for a diagnostic detection, even interfere with said detection or are undesired for other reasons. A person skilled in the art is capable of developing and preparing suitable wash solutions, for example physiological saline solutions such as PBS buffer or buffer having a low salt concentration, for example 50 mM potassium phosphate, pH 7. Wash solutions can also contain surface-active substances such as alcohols, detergents and surfactants for removing hydrophobic contaminants. Especially in the case of upcoming longer storage or for disinfection, it is also possible to use antimicrobial substances such as azide or ethanol.

In a further preferred embodiment, the at least one liquid or the second liquid is a liquid which contains substances required for the detection reaction. For example, if the immobilized reaction partner and the reactant are, respectively, an antigen and an antibody which binds thereto, then after formation of the antigen/antibody complex, a solution containing a second, enzyme-labeled or fluorescently labeled antibody can be introduced into the device according to the invention, and so a detectable complex is present immobilized on the microscope slide. In a preferred embodiment, the at least one or second liquid comprises a dye which stains a tissue section immobilized on the adhesion surface or prokaryotic or eukaryotic cells or preparations immobilized on the adhesion surface.

The immobilization of the reaction partner can be reversible or irreversible, so long as said immobilization is sufficiently resistant for the performance of the method according to the invention. Preferably, the reaction partner is immobilized via at least one covalent chemical bond. A person skilled in the art is aware of numerous methods for immobilizing molecules on surfaces of very widely differing nature. For example, proteins can be immobilized via chemical activation on carbohydrate, glass or polymer surfaces, as described in US20100056764 or in U.S. Pat. No. 5,137,765 for example. Alternatively, a fixation can be achieved via a sufficiently strong ionic or hydrophobic interaction. For example, a protein with a negative charge can bind with a high affinity to an inorganic surface with a positive charge, as described in U.S. Pat. No. 4,206,286 for example.

The device according to the invention makes it possible for the liquid from the liquid reservoir to reach the upper side of the elevation through the escape opening via a feed element by means of a pumping device in order to come into contact with the adhesion surface. The duration of the contact and the conditions under which said contact takes place can be varied depending on the nature and function of the liquid. If the liquid is a liquid containing reactants which are dissolved therein and which are to bind to or react with the immobilized reaction partner, the contact must last for a sufficiently long time so that a sufficient number of molecules of the reactant can interact with the immobilized reaction partner and, for example, form a detectable complex. For example, the contact can last at least 10 seconds, 30 seconds, one, two, five, ten, 15, 30, 60, 120 or 180 minutes. If the liquid is a wash liquid, a short contact may suffice.

Depending on the requirements, the liquid can be introduced into the device according to the invention in a continuous or discontinuous manner, i.e., in thrusts, according to which the pumping process is interrupted. If the liquid is a liquid of which only small volumes are available, for example a blood sample of human or animal origin, the available amount can be introduced and the feed can be interrupted after the adhesion surface has been sufficiently wetted. During the following incubation, the interaction between reaction partner and reactant can then take place. However, if the liquid is a wash solution, it can be introduced continuously in relatively large amounts in order to thoroughly wash the adhesion surface of the microscope slide.

The liquid that has reached the upper side of the elevation accumulates, so long as its volume does not exceed the volume which can be held between adhesion surface and upper side of the elevation, for example by means of hydrophilic interactions between liquid and adhesion surface and also upper side of the elevation. In a preferred embodiment, the escape opening on the upper side of the elevation, the upper side of the elevation and the adhesion surface are designed such that the at least one liquid flows tangentially along the immobilized reaction partner when said liquid is introduced into the device. If more liquid is introduced than can be held between adhesion surface and upper side of the elevation, said liquid runs on the elevation toward the sides onto the base of the trough and can drain via a drain opening, if present. Liquid in contact with the adhesion surface can also be removed by evaporation, optionally quickened by application of negative pressure to the trough if it is sealable in a pressure-tight manner, or by displacement via a further introduced liquid or by blowing-in of a gas.

Liquid in contact with the adhesion surface can also be actively aspirated via the escape opening and the channel opening thereinto. The liquid can then be fed back into the liquid reservoir or, particularly preferably, removed from the device via its own drain on the feed element and discarded, reused or stored.

In a preferred embodiment, the adhesion surface on the microscope slide has an elongated shape, as described in a different connection in the prior art, for example in EP 2 191 893. In the case of a trough having a rectangular base, the adhesion surface can be arranged along or perpendicularly to the longitudinal axis of the trough. In a particularly preferred embodiment, the elevation, matching such an elongated shape of the adhesion surface, is designed as a groove such that the elongated adhesion surface on the microscope slide is opposite it and the at least one liquid, upon introduction via the feed element in the direction of the escape opening, comes into contact with the reaction partner immobilized on the adhesion surface. Optionally, the elevation designed as a groove has at least two channels, each having an escape opening, it being possible for one of the channels to be used to supply the liquid and for the other to be used to pump away the liquid; particularly preferably, there is then an escape opening at each of the two ends of the groove. Alternatively, the groove can also have a series of escape openings which are evenly distributed across the longitudinal axis of the groove.

The device according to the invention can be used to carry out a method comprising the contacting of an immobilized reaction partner with at least one liquid.

Depending on the problem and the properties of the immobilized reaction partner and of the reactant, it is possible to carry out individual, but also all steps of the detection method using the device according to the invention, if necessary by using various liquids in any order.

In any case, it is necessary to provide the device according to the invention comprising the microscope slide with the immobilized reaction partner on the adhesion surface. In this connection, in a preferred embodiment, the immobilization can even take place in the device according to the invention. To this end, the microscope slide containing the adhesion surface, but not containing immobilized reaction partner, is inserted into the device according to the invention. Subsequently, a liquid comprising the reaction partner to be immobilized and optionally further substances required for the immobilization is introduced into the device via the channel in the elevation until said liquid is in contact with the adhesion surface, and so immobilization of the reaction partner occurs. The liquid is then removed, for example by aspiration or by displacement by introduction of another liquid, for example a wash solution. Alternatively, the reaction support can be immobilized outside the device according to the invention, followed by insertion of the microscope slide into the device according to the invention.

If required by the chemical properties of the adhesion surface and of the reaction partner to be immobilized, the adhesion surface can, prior to immobilization, be additionally contacted with a further liquid comprising at least one activating substance which chemically activates chemical groups present on the adhesion surface such that the subsequent immobilization proceeds more efficiently or to a sufficient extent in the first place.

After the two aforementioned steps, more precisely the actual immobilization of the reaction partner and a chemical activation of the adhesion surface to be optionally carried out beforehand, and also after other steps in which a liquid containing substances which can interact with the adhesion surface and molecules immobilized thereon is introduced into the device according to the invention, it is advisable to carry out a wash step. In the simplest case, this is achieved by introducing a wash solution into the device according to the invention until the adhesion surface containing the immobilized reaction partner and/or all the components of the device according to the invention that come into contact with introduced liquids have been sufficiently cleaned. Prior to the first-time use of new instruments or parts thereof, more particularly prior to the first-time use of microscope slides and/or readymade substrates, or for the preparation of the device according to the invention for a new experiment, a wash step may also be advisable in order to remove liquids containing substances which originate from previous experiments or are used for the storage and/or the transport of new instruments or parts thereof and might have an interfering effect during actual use.

The introduction of the wash solution can continue until the device according to the invention has been completely cleared of contaminants. In a preferred embodiment, the term "completely cleared of contaminants", as used here, is understood to mean that, when wash solution is further introduced into the device, there are no more detectable contaminants in the wash solution escaping from the device after the wash step.

If the reaction partner is not to be immobilized within the device according to the invention, this can be done before the insertion of the microscope slide into the device according to the invention. This is especially advisable when the reaction partner to be immobilized is present in a low amount and/or in a small volume. In this case, introduction into the device according to the invention can lead to a high loss of reaction partner, for example when it is nonspecifically adsorbed by surfaces, for example in the channel, or highly diluted and only a small part thereof gets as far as the adhesion surface and can be immobilized thereon. After the immobilization, the microscope slide is inserted into the holding device of the device according to the invention and can be contacted therein with any further liquids, for example with a liquid comprising a reactant. Even after an immobilization not carried out within the device according to the invention, it is possible for the microscope slide to be washed. This can also be done outside the device according to the invention or within the device by introduction of wash solution.

It is also possible for the contacting of the immobilized reaction partner with the reactant to take place within or outside the device. If the immobilized reaction partner is immobilized within the device according to the invention, but the contacting with the reactant is to take place outside, then the microscope slide must be removed for this purpose. Again, a contacting outside the device is especially advisable when the reactant is present in a low amount and/or in a small volume, for example when the reactant in a blood sample from an infant is to be determined.

A further particular strength of the device according to the invention and of the method according to the invention that is carried out therewith is that it is possible to successively introduce multiple liquids containing, in each case, a component required for a detection reaction, without additional manual work being generated. In the case of a manual process, many users tend in practice not to let the various components react successively via separate liquids, but instead in fewer steps, preferably a single step, containing a mix of components. Especially in the area of indirect immunofluorescence, the introduction of reagents in succession leads to qualitatively better results. For example, if antibodies of multiple immunoglobulin classes (IgA, IgG and IgM) are to be determined in a sample, a sequential incubation with fluorescently labeled secondary antibodies against IgA, IgG and IgM generally leads to more unambiguous reactions than is the case when incubation is carried out with one reagent mix. A further particular strength of the present invention is that a liquid in contact with the adhesion surface is not only introduced via the channel in the elevation, but can also be removed by aspiration. In this way, a liquid which is to be reused after the contacting with the adhesion surface can be recovered separately for each elevation and, if required, stored and/or used for other applications, for example other analytical methods, without there being the possibility of a mixing with liquids from other batches.

The option to aspirate the liquid also makes it possible to carry out chemical detection reactions, especially chromogenic color reactions, for example for the detection of an enzymatically active reactant or of an enzyme-labeled second antibody, in the device according to the invention and to then evaluate them. For this purpose, it is possible, after formation of the complex comprising the immobilized reaction partner and the enzymatically active reactant or the enzyme-labeled second antibody, to introduce a liquid comprising a chromogenic substrate into the device according to the invention until it is in contact with the adhesion surface and the substrate can be converted enzymatically. After an appropriate incubation period, it can be aspirated and examined in a detection device, for example in a UV-visible spectrometer in the case of the chromogenic substrate. In a particularly preferred embodiment, the device according to the invention itself is provided with such a detection device. For example, the liquid-filled interspace between the adhesion surface and the upper side of the elevation can be irradiated from one side with electromagnetic radiation of an appropriate wavelength and the absorption of the radiation in the liquid can be measured on the other side of the elevation. Alternatively, the aspirated liquid can be conducted into a detection device connected to the channel or the feed element and measured therein.

In a particularly preferred embodiment, within the or outside the device according to the invention after the introduction of the first, second or further liquid or the wash solution, the microscope slide is subjected to a further step of f) drying the adhesion surface. The drying is preferably achieved by the microscope slide being moved by means of the holding device, preferably along the longitudinal axis of the trough, until the adhesion surface is dried by the air stream of at least one air nozzle optionally belonging to the configuration of the device according to the invention. Preferably, pressurized air is conducted through the air nozzle.

In a further, particularly preferred embodiment, within the or outside the device according to the invention after the introduction of the first, second or further liquid or the wash solution or the further step f), the microscope slide is appropriately prepared for the evaluation, for example by application of mounting medium, for example phosphate-buffered saline solution admixed with glycerol, and placement of a coverslip.

In a preferred embodiment, the method according to the invention is used to carry out an ELISA assay which can detect autoantibodies in a human blood sample. For this purpose, an antigen recognized by the autoantibody, for example a polypeptide, in purified form or in the form of a cell or a tissue is immobilized on the adhesion surface of the microscope slide as immobilized reaction partner. The adhesion surface is then washed and contacted with the human blood sample which is to be examined and which may contain the autoantibody (reactant), followed by a further wash step. Thereafter, the adhesion surface containing the immobilized antigen is contacted with a solution containing a second antibody which binds to the autoantibody and has a label for the detection of the complex composed of antigen, autoantibody and second antibody, in the case of the ELISA an active enzyme, for example a peroxidase. Lastly, the microscope slide can be removed from the device according to the invention and treated with a chromogenic substrate of the peroxidase. A positive color reaction indicates the presence of the autoantibody.

A person skilled in the art is aware of numerous variants of the ELISA assay, which variants can likewise be carried out as part of the method according to the invention. For example, in the case of the sandwich ELISA, a first antibody (reaction partner) which recognizes an antigen (reactant) to be detected in a human sample can be firstly immobilized on the adhesion surface. The detection is then achieved via a second antibody which likewise binds to the reactant.

Alternatively, the method according to the invention can be used for the immunofluorescence-based detection of autoantibodies. The procedure is carried out as for the ELISA assay, apart from the fact that the second antibody has been labeled with a fluorescent molecule, for example with fluorescein. In this case, the complex composed of antigen, autoantibody and second antibody is detected using a fluorescence microscope.

Alternatively, the method according to the invention can be used for the detection of specific nucleic acid sequences, for example of PCR products which are obtained starting from a human sample containing, as template, a nucleic acid to be detected. In this case, the immobilized reaction partner used is a nucleic acid which specifically binds to the nucleic acid sequence to be detected (reactant). The contacting of immobilized reaction partner and reactant then takes place under conditions which allow a specific binding. Such conditions can be routinely found by a person skilled in the art. For the detection of the complex composed of immobilized reaction partner and reactant, routinely usable methods are likewise available, for example detection via fluorescence.

Hereinbelow, the invention will be elucidated by means of exemplary embodiments with reference to the figures. The embodiments described are, in all respects, merely exemplary and not to be understood as limiting, and various combinations of the features mentioned are covered by the scope of the invention.

As is evident from said figures, the teaching according to the invention can be carried out using a device for contacting at least one immobilized reaction partner (1) with at least one liquid (2), comprising a trough (3) having a base (4) from which at least one elevation (5) having an upper side (6) projects into the interior of the trough (3), wherein the at least one elevation (5) has a channel (7) which runs perpendicularly to the base (4) of the trough (3) and opens into at least one escape opening (8) on the upper side (6) of the elevation (5), wherein the channel (7) is fed from at least one liquid reservoir (11) containing the at least one liquid (2) via a feed element (9) by means of a pumping device (10), a holding device (12) which detachably holds a microscope slide (13) having at least one adhesion surface (14) containing the at least one immobilized reagent (1), such that the adhesion surface (14) is facing the interior of the trough (3), wherein the upper side (6) of the elevation (5) and the adhesion surface (14) are positioned relative to one another such that liquid escaping from the escape opening (8) is in contact with the immobilized reagent.

Figure 1:
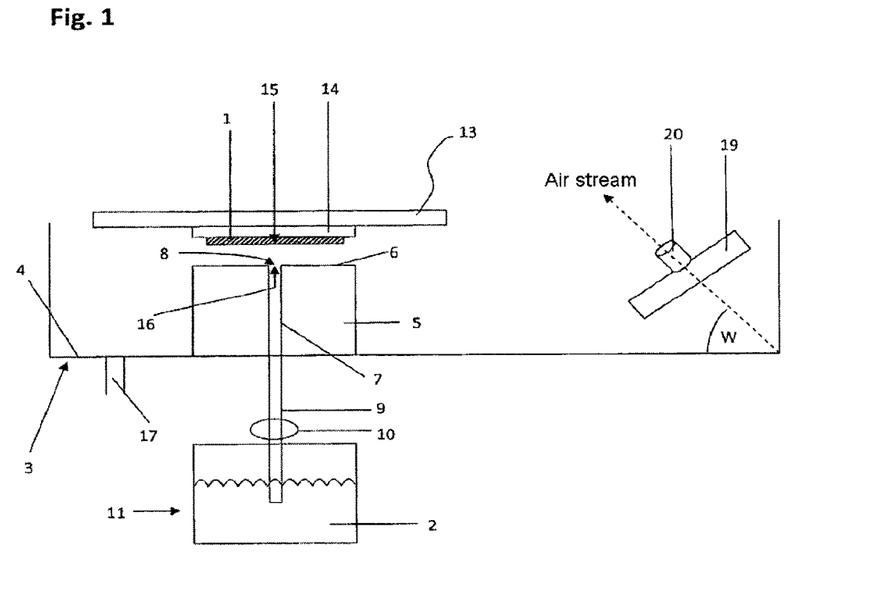
FIG. 1 shows a device according to the invention from the side, perpendicular to the longitudinal axis of the device.
Figure 2:
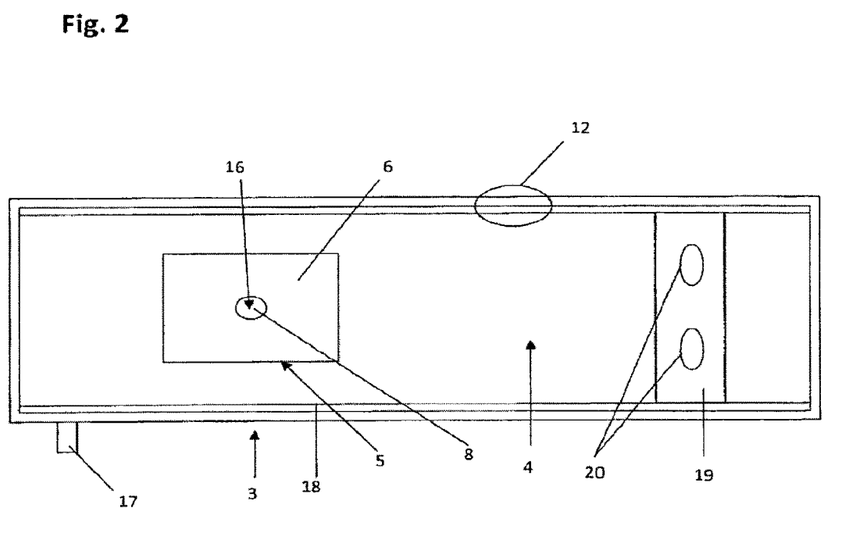
FIG. 2 shows the device according to the invention from above.
Figure 3:
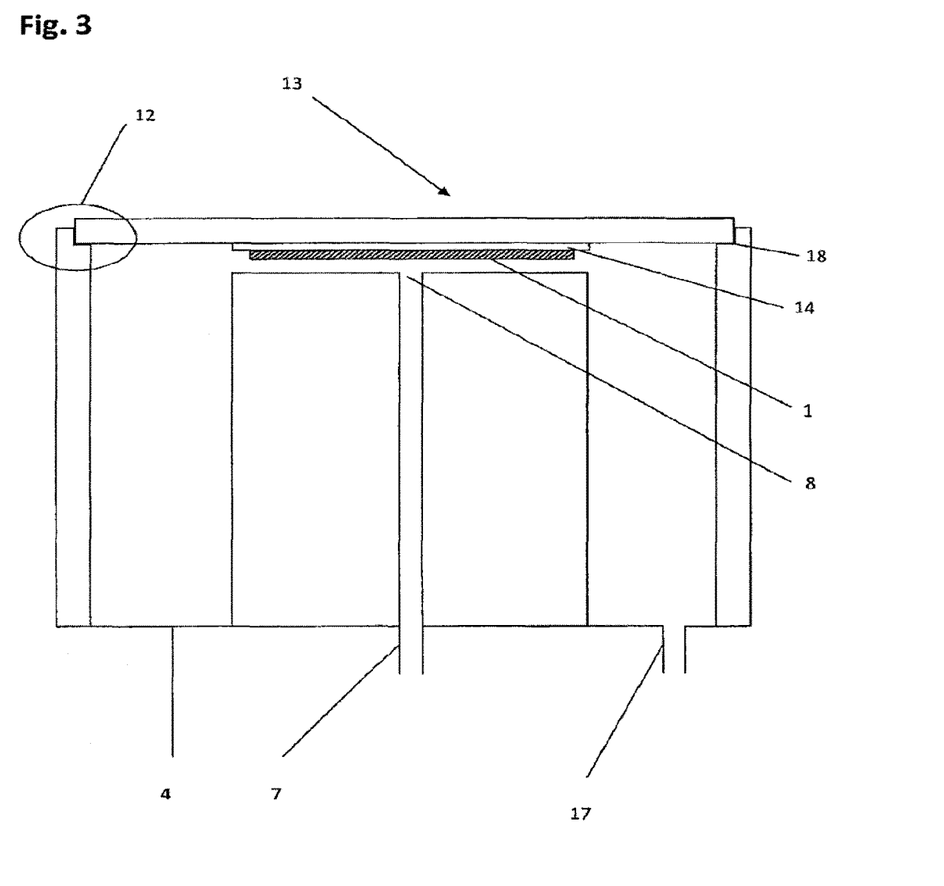
FIG. 3 shows the device according to the invention from the front, along the longitudinal axis of the device.

Preferably, the adhesion surface (14) has a central point (15) and the upper side (6) of the elevation (5) has a central point (16), wherein the upper side (6) of the elevation (5) and the adhesion surface (14) are positioned such that the central point (15) of the adhesion surface (14) and the central point (16) of the upper side of the elevation (5) are on a line running perpendicular to the longitudinal axis of the trough (3).

Preferably, the trough (3) has at least one drain opening (17).

Preferably, the holding device (12) allows a movement of the microscope slide (13) along the longitudinal axis of the trough (3), particularly preferably over a groove (18) or rail applied to the upper edges of the trough (3).

Preferably, the trough is further provided with at least one air nozzle (20), on a support (19) used to position the air nozzle, for drying the adhesion surface (14), wherein, particularly preferably, the air stream from the at least one air nozzle (20) forms an angle (W) of less than 90 degrees, preferably from 20 to 70 degrees, with the plane determined by the base (4) of the trough (3).

Figure 4A:
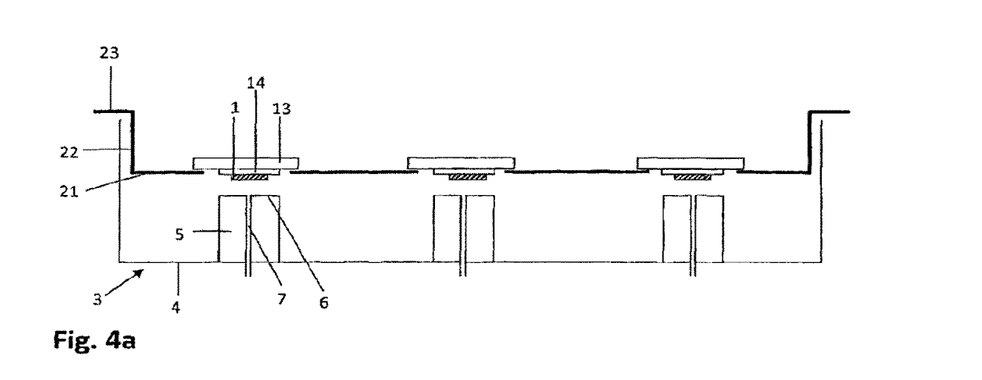
FIGS. 4a, 4b and 4c show the device according to the invention comprising a preferred holding device, from the side, perpendicular to the longitudinal axis of the device (FIG. 4a), in transverse section, along the longitudinal axis of the device (FIG. 4b), and from above (FIG. 4c), with some details not being shown for the sake of clarity.
Figure 4B:
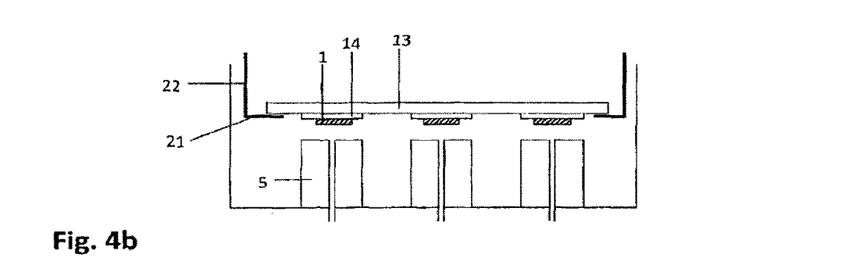
Figure 4C:
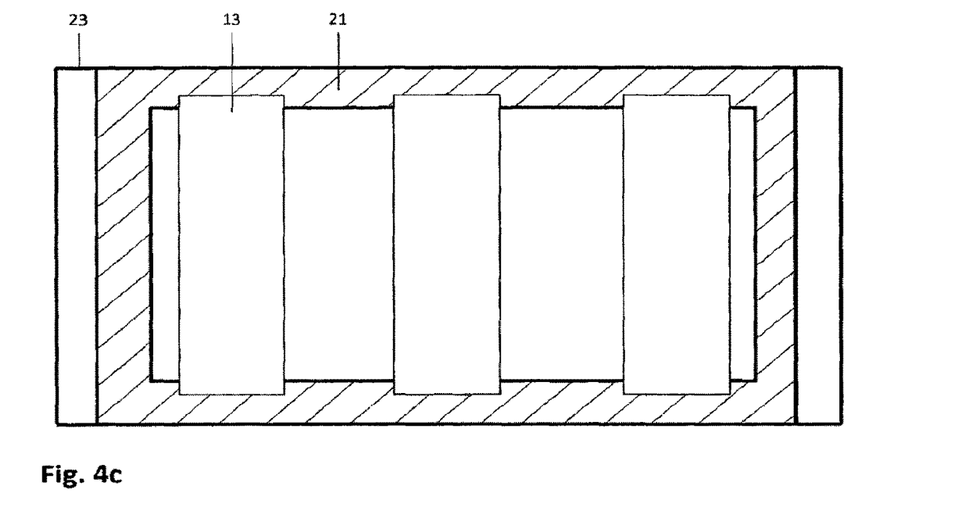

Preferably, the device according to the invention is provided with a holding device which comprises a frame (21), at least two lateral walls (22) arising on opposing sides of the frame, and a handle (23).

LIST OF REFERENCE SIGNS (1) Reagent
(2) Liquid
(3) Trough
(4) Base
(5) Elevation
(6) Upper side of the elevation
(7) Channel
(8) Escape opening
(9) Feed element
(10) Pumping device
(11) Liquid reservoir (12) Holding device
(13) Microscope slide
(14) Adhesion surface
(15) Central point of the adhesion surface
(16) Central point of the elevation
(17) Drain opening
(18) Groove
(19) Support
(20) Air nozzle
(21) Frame
(22) Lateral end of the holding device
(23) Handle

REFERENCES

1. Objektträger [Microscope slide]. German utility model DE 20 2011 005 278
2. Stöcker W. Verfahren und Vorrichtungen für Untersuchungen an unbeweglich gemachtem biologischen Material [Processes and devices for examinations on immobilised biological material]. European patent EP 0 117 262
3. Stöcker W., Rateike M., Morrin M. Verfahren zur Herstellung Festphasen-gebundener Bioreagenzien [Method for producing solid-phase bonded bioreagents]. International patent application WO2005073693
4. Ursoe B., Reumert Wagtmann P. A., Pedersen I. L., Svensson A. Antibodies against human NKG2D and uses thereof. US patent application US 20100056764
5. Stöcker W., Rateike M., Maltzahn B., Behring R. Analyseverfahren und Vorrichtung für biologische Reaktionen zwischen einer flüssigen und einer festen Phase [Analysis method and devices for biological reactions between a liquid and a solid phase]. European patent application EP 2 191 893
6. Becker, H. D., Einsle, X. Device and method for wetting objects. US patent application US 2006239858.
7. Farnsworth V. Derivatized glass supports for peptide and protein sequencing. U.S. Pat. No. 5,137,765
8. Keyes M. H. Immobilization of proteins on inorganic supports. U.S. Pat. No. 4,206,286

The invention claimed is:
1. A device, comprising:
(i) a trough having a base from which at least one elevation having an upper side projects from the base into the interior of the trough,
wherein the at least one elevation has a channel which runs from the base of the trough to the upper side of the elevation, and opens into at least one escape opening on the upper side of the elevation,
wherein the channel is fed from at least one liquid reservoir containing at least one liquid via a feed element by a pumping device, and
(ii) a holding device configured to detachably hold at least one microscope slide having at least one adhesion surface containing an immobilized reaction partner, such that the adhesion surface is facing the interior of the trough, and that the upper side of the elevation and the adhesion surface are positioned relative to one another such that liquid escaping from the escape opening is in contact with the immobilized reagent,
wherein the device is suitable for contacting the immobilized reaction partner with the at least one liquid such that excess liquid trickles down from the at least one elevation; and
wherein said base has at least eight elevations.

2. The device as claimed in claim 1, wherein the channel is additionally fed from a further liquid reservoir containing a second liquid.
3. The device as claimed in claim 1, wherein the channel opens into more than one escape opening on the upper side of the elevation.
4. The device as claimed in claim 1, wherein the adhesion surface has a central point and the upper side of the elevation has a central point, and wherein the central point of the adhesion surface and the central point of the upper side of the elevation are opposite each other.
5. The device as claimed in claim 1, wherein the trough has at least one drain opening.
6. The device as claimed in claim 1, wherein the pumping device allows any liquid which is in contact with the immobilized reaction partner to be aspirated from the direction of the escape opening.
7. The device as claimed in claim 1, wherein the escape opening on the upper side of the elevation, the upper side of the elevation and the adhesion surface are designed such that the at least one liquid flows tangentially along the immobilized reaction partner when said liquid is introduced into the device.
8. The device as claimed in claim 1, wherein the holding device comprises a frame equipped to accommodate and to hold at least one microscope slide, wherein, after accommodation, the adhesion surface is situated on that side of the microscope slide which is resting on the frame.
9. The device as claimed in claim 8, wherein the frame has at least one lateral wall optionally provided with a handle.
10. The device as claimed in claim 9, wherein the lateral wall of the frame has a profile suited to positioning the holding device and thus the adhesion surface in the device.
11. The device according to claim 1, comprising one or more microscope slides inserted into the holding device, wherein at least one of said microscope slides comprise at least two adhesion surfaces.
12. The device according to claim 1, further comprising (iii) one or more microscope slides inserted into the holding device.
13. The device as claimed in claim 12, wherein the holding device allows a movement of the one or more microscope slides.
14. The device as claimed in claim 13, wherein the trough is further provided with at least one air nozzle configured for drying the adhesion surface.
15. The device as claimed in claim 12, further comprising a transport device which allows the insertion of the one or more microscope slides into the device.
16. The device according to claim 1, wherein said elevation has an upper side and a lower side wherein said lower side of said elevation is in direct contact with said trough.
17. A method for contacting an immobilized reaction partner with at least one liquid, comprising:
introducing the at least one liquid to the device of claim 1, comprising at least one microscope slide containing the immobilized reaction partner, in the direction of the escape opening via the feed element until the at least one liquid is in contact with the immobilized reaction partner.
18. The method as claimed in claim 17, further comprising:
introducing a second liquid and optionally a further liquid in the direction of the escape opening via the feed element until the second liquid is in contact with the immobilized reaction partner.

19. The method as claimed in claim 17, further comprising:

introducing a wash solution in the direction of the escape opening via the feed element until the wash solution is in contact with the immobilized reaction partner, wherein the introducing of the wash solution can be carried out before and/or after the introducing of the at least one liquid.

20. The method as claimed in claim 19, wherein the introducing of the wash solution is carried out until the device has been completely cleared of contaminants.

21. The method as claimed in claim 17, wherein the introducing of the at least one liquid, the second liquid and optionally further liquid and/or wash solution is followed by aspirating the at least one or second and optionally further liquid or the wash solution from the immobilized reaction partner from the direction of the adhesion surface via the channel.

22. The method as claimed in claim 17, wherein the at least one microscope slide is accommodated in the holding device, and the holding device is inserted into the device.

23. A device, comprising:

(i) a trough having a base from which at least one elevation having an upper side projects from the base into the interior of the trough, said base being surrounded by upright walls extending above said at least one elevation, wherein the at least one elevation has a channel which runs from the base of the trough to the upper side of the elevation, and opens into at least one escape opening on the upper side of the elevation, wherein the channel is fed from at least one liquid reservoir containing at least one liquid via a feed element by a pumping device, and (ii) a holding device configured to detachably hold at least one microscope slide having at least one adhesion surface containing an immobilized reaction partner, such that the adhesion surface is facing the interior of the trough, and that the upper side of the elevation and the adhesion surface are positioned relative to one another such that liquid escaping from the escape opening is in contact with the immobilized reagent, wherein the device is suitable for contacting the immobilized reaction partner with the at least one liquid such that excess liquid trickles down from the at least one elevation.

24. The device as claimed in claim 23, wherein the channel is additionally fed from a further liquid reservoir containing a second liquid.

25. The device as claimed in claim 23, wherein the channel opens into more than one escape opening on the upper side of the elevation.

* * * * *